United States Patent [19]

Halling

[11] Patent Number: 5,552,476

[45] Date of Patent: Sep. 3, 1996

[54] HYDROLYZED SILANE EMULSIONS AND THEIR USE AS SURFACE COATINGS

[75] Inventor: Robert A. Halling, Wilmington, Del.

[73] Assignee: E. I. Du Pont de Nemours and Company, Wilmington, Del.

[21] Appl. No.: 248,613

[22] Filed: May 12, 1994

Related U.S. Application Data

[63] Continuation-in-part of Ser. No. 206,779, Mar. 4, 1994.

[51] Int. Cl.$^6$ ............... C08J 3/03; C08J 3/07; B05D 1/00; B01F 17/54
[52] U.S. Cl. ............ 524/837; 524/858; 106/287.12; 427/387
[58] Field of Search .................. 524/837, 858; 106/287.12; 427/387

[56] References Cited

U.S. PATENT DOCUMENTS

| | | | |
|---|---|---|---|
| 2,476,307 | 7/1949 | Klein et al. | 260/448.8 |
| 3,012,006 | 12/1961 | Holbrook et al. | 260/46.5 |
| 3,422,131 | 1/1969 | Pittman et al. | 260/448.2 |
| 3,442,664 | 5/1969 | Heine | 106/2 |
| 3,450,738 | 6/1969 | Blochl | 260/448.8 |
| 4,024,306 | 5/1977 | Takamizawa et al. | 427/387 |
| 4,089,882 | 5/1978 | Takamizawa et al. | 260/448.2 |
| 4,342,796 | 8/1982 | Brown et al. | 427/136 |
| 4,478,911 | 10/1984 | Price | 428/332 |
| 4,525,213 | 6/1985 | Linn | 106/2 |
| 4,525,425 | 6/1985 | Church | 428/428 |
| 4,549,003 | 10/1985 | Lim et al. | 528/42 |
| 4,648,904 | 3/1987 | DePasquale et al. | 106/2 |
| 4,687,707 | 8/1987 | Matsuo et al. | 428/336 |
| 4,689,181 | 8/1987 | Blatch | 260/408 |
| 4,865,910 | 9/1989 | Inoguchi et al. | 428/268 |
| 4,874,431 | 10/1989 | Fey et al. | 106/2 |
| 4,877,654 | 10/1989 | Wilson | 427/387 |
| 4,889,747 | 12/1989 | Wilson | 427/221 |
| 4,983,459 | 1/1991 | Franz et al. | 428/410 |
| 4,990,377 | 2/1991 | Wilson | 427/387 |
| 5,011,963 | 4/1991 | Ogawa et al. | 556/485 |
| 5,051,129 | 9/1991 | Cuthbert et al. | 106/2 |
| 5,059,649 | 10/1991 | Maxson et al. | 524/398 |
| 5,124,467 | 6/1992 | Rodgers et al. | 556/427 |
| 5,274,159 | 12/1993 | Pellerite et al. | 556/485 |

OTHER PUBLICATIONS

Tailoring Surfaces With Silanes, Chemtech Dec. 1977, pp. 766–778.

Alastair W. Stupart, Water Repellent Treatments For Brickwork, Oct. 1993 pp. 809–811.

*Primary Examiner*—Margaret Glass

[57] ABSTRACT

Novel and highly reactive hydrolyzed silane emulsions are achieved by emulsifying a hydrolyzable alkoxysilane (e.g., or the like) in water in the presence of an effective amount of an emulsifier of sufficiently high HLB value (preferably 14 or greater) to simultaneously retain said hydrolyzable alkoxysilane compound in a substantially totally hydrolyzed state and inhibit said resulting hydrolyzed alkoxysilane compound from self-condensation. Such reactive emulsions containing hydrocarbon silanes are useful to produce durable coatings that impart water repellency and lubricity to substrates having siliceous, cellulosic or proteinaceous surfaces.

10 Claims, No Drawings

HYDROLYZED SILANE EMULSIONS AND THEIR USE AS SURFACE COATINGS

CROSS-REFERENCE TO RELATED APPLICATION

This application is a continuation-in-part of U.S. Ser. No. 08/206,779 filed Mar. 4, 1994, herein incorporated by reference.

BACKGROUND OF THE INVENTION

1. Field of the Invention

The present invention relates to stable aqueous emulsions of hydrolyzed silanes and their application to various substrates to impart water repellency and lubricity. More specifically but not by way of limitation, the present invention relates to aqueous emulsions of a silane and an effective amount of an emulsifier having a hydrophile-lipophile balance, HLB, sufficiently high to retain the silane in a stable aqueous emulsion in substantially a hydrolyzed state.

2. Description of the Related Art

It is known that hydrolyzable silanes can be applied to surfaces to impart hydrophobic or water repellency properties (see, B. Arkles, Chemtech, 1977, 766). These silanes are applied to the surfaces either dissolved in a volatile organic solvent or as aqueous solutions or emulsions. With the solvent based products, the solvent must be evaporated once the solution is applied to the surface. In addition, the hydrolyzable silane must be contacted with water or sufficient adsorbed moisture on the surface being treated to hydrolyze the silane so that it may chemically bond to the surface to form a durable coating (see for example, U.S. Pat. Nos. 4,342,796 and 4,525,213). The presence of volatile solvents in coating formulations is generally harmful to the environment and may be hazardous due to their flammability. In addition, treatments of surfaces with these hydrolyzable silanes frequently require the use of elevated temperatures and certain catalysts to accelerate the hydrolysis of the silane and the condensation with the surface to achieve the desirable effects (see for example, U.S. Pat. Nos. 4,478,911 and 4,874,431).

When the hydrolyzable silanes are applied from the more preferred aqueous solutions or emulsions, buffers must be added to the aqueous mixtures to maintain the pH of the mixture within narrow limits to prevent premature hydrolysis of the silane and subsequent self-condensation to a polymeric polysiloxane (see for example, U.S. Pat. Nos. 4,889,747 and 4,990,377). Such a polymeric structure is no longer dispersible in the aqueous medium, and contains a reduced number of active sites that can bond the silane to the substrate. Generally acidic or basic conditions will accelerate this hydrolysis. However, if the aqueous emulsion is stabilized with a buffer to prevent hydrolysis on storage, this buffer must be overcome once the silane is applied to the substrate to now permit the hydrolysis to take place, and bonding with the substrate to occur. The prior art therefore teaches that for the preferred aqueous systems, the silane must be retained in the emulsions in a non-hydrolyzed state to achieve adequate storage stability, and that hydrolysis must then be caused to take place when the silane is applied to the substrate so that the proper bonding can occur between the silane composition and the surface to produce the desirable properties.

SUMMARY OF THE INVENTION

In view of the above and unlike the solvent based hydrolyzable silanes and the buffer-stabilized aqueous trialkoxsilane emulsions of the prior art it has now been discovered that the aqueous silane emulsions of this invention contain the silane in an essentially completely hydrolyzed state and thus ready for instant bonding to the substrate to provide repellency and lubricity properties. Notwithstanding this apparent total hydrolysis and thus highly reactive state of the silane, the unique aqueous emulsions of the instant invention do not permit the hydrolyzed silanes to self-condense to high molecular weight, water insoluble, polysiloxane structures while in this emulsified state. Thus these emulsions are generally stable to long periods of storage of one year or more, are stable to broad ranges of pH, typically from a pH of 2.0 or less to about 11.0, are stable to temperatures of 80° C. or greater, and frequently are stable to repeated freezing and thawing conditions without undergoing coagulation and precipitation of the silane.

In the broadest sense of the above observed high reactivity of the emulsion, wherein apparently total hydrolysis of the silane compound in the micelle is achieved simultaneously with long term inhibition of the self-condensation reaction, is felt to be characteristic of the use of any readily emulsifiable alkoxysilane in combination with an effective amount of an emulsifier of very high HLB value. Thus, the present invention provides for novel aqueous emulsions of unique reactivity and stability comprising: (a) an alkoxysilane compound emulsifiable in water; and (b) an effective amount of an emulsifier of sufficiently high HLB value to simultaneously retain the alkoxysilane compound in a hydrolyzed state and inhibit the hydrolyzed alkoxysilane compound from self-condensation.

In one specific embodiment of this invention and consistent with the acknowledged prior art recognition that durability is associated with the presence of multiple hydrolyzable groups leading to cross-linked siloxane structures upon condensation with a substrate, the present invention further provides for a trialkoxysilane of the following formula be employed:

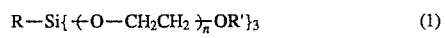  (1)

Wherein: R is a hydrocarbon radical of 8 to 24 carbons; R' are the same or different alkyl radicals of 1 to 3 carbon atoms; and n=2 to 10.

The improved method of using the emulsion for surface coating of a substrate according to the instant invention comprises the steps of:

(a) emulsifying in water (i) an alkoxysilane represented by the formula:

where R is a hydrocarbon radical of 8 to 24 carbons; R' are the same or different alkyl radicals of 1 to 3 carbon atoms; and n=2 to 10 and (ii) an effective amount of an emulsifier of sufficiently high HLB value to simultaneously retain said alkoxysilane compound in a hydrolyzed state and inhibit said hydrolyzed alkoxysilane compound from self-condensation thus forming a reactive aqueous emulsion; and (b) contacting a substrate with said reactive aqueous emulsion of step (a).

One object of this invention is to produce aqueous emulsions of selected hydrolyzable silanes and/or hydrolyzable alkoxy substituted silanes that exhibit good stability on storage under a broad range of pH conditions. Another object is to provide such aqueous emulsions wherein the hydrolyzable silane is retained in a highly reactive state by virtue of essentially total hydrolysis of the alkoxy moiety and, simultaneously, self-condensation is inhibited. Still another object of this invention is to provide an improved process that takes advantage of the highly reactive state of the silane in the emulsion to render substrates water repellent and to impart a high lubricity surface that significantly reduces the tendency to scratch by the application of the aqueous emulsions of the hydrolyzed silanes without the need for special curing operations.

DESCRIPTION Of THE PREFERRED EMBODIMENTS

In describing and exemplifying the various features and aspects of the present invention and in explaining how the present invention differs from and is distinguishable over the previously known compositions and methods of use along with their corresponding advantages, it should be appreciated that the novelty of the present invention should be viewed as being the composite of achieving a highly reactive yet stable aqueous emulsion capable of producing a durable, chemically bonded coating as opposed to the specific properties resulting from the simple coating of the substrate. Even though a specifically preferred embodiment of this invention relates to stable aqueous emulsions of hydrolyzable reactive silanes that are storage stable and that react with the substrate surfaces to impart water repellency and lubricity, in a broader sense the invention relates generically to any desirable property associated with the silane coating. As such, the following description will utilize the preferred silanes that encompass essentially all of these features with the understanding that certain features of the invention have much broader implications and as such the specific embodiment should not be interpreted as being unduly limiting.

Aqueous emulsions of formula (1), in addition to imparting water repellency to surfaces coated therewith, also impart improved lubricity. Generally, desired lubricity is observed for compounds wherein R contains at least 8 carbon atoms and is particularly true of those compounds wherein R contains 16 or more carbon atoms. This increased lubricity is of course more readily observed if the substrate coated has a smooth surface. This increased lubricity, that is, decreased coefficient of friction, renders the surface much more scratch resistant, a particularly important benefit for glass and tile surfaces.

The silanes useful in this invention are represented by the following formula:

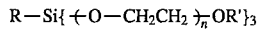  (1)

wherein: R is a hydrocarbon radical of 8 to 24 carbons; R' are the same or different alkyl radicals of 1 to 3 carbon atoms; and n=2 to 10. The preferred compositions are R= one or more hydrocarbon radicals of 16 to 24 carbon atoms; R'=methyl; and n=2 to 10. Especially preferred, because of low cost of the starting materials and high efficiency in imparting desirable scratch resistance to treated surfaces is R=$C_{18}$ hydrocarbon radical; R'=methyl; and n=2 or 3.

The silanes of this invention are prepared by methods known in the art (see Kirk-Othmer, Encyclopedia of Chemical Technology, Third Edition, Vol. 20, and R. C. Mehrota, Pure And Applied Chem., 13, 111, 1966). The preferred method is by reacting the corresponding trichlorosilane with the proper ether alcohol, such as diethylene glycol monomethyl ether or triethylene glycol monomethyl ether, for example, according to the following equation:

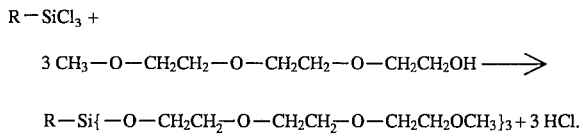

An alternate method also useful for the preparation of the preferred silanes for this invention involves the transesterification of the corresponding alkyltrimethoxy or alkyltriethoxy silanes with the ether alcohol, with removal of the methanol or ethanol byproduct. This reaction usually requires an acid or base catalyst, such as p-toluenesulfonic acid or sodium methoxide, to accelerate the reaction.

Any solvent inert to the reactants and products may be used in the reaction to provide the hydrocarbonsilane ether alkoxides of this invention. If the reactants and products are liquid and mutually miscible under the reaction conditions, the solvent may be omitted. Solvents such as hexane, heptane, toluene and cyclohexane are suitable.

The temperatures suitable for these reactions are those that will effect completion within a reasonable length of time. Temperatures ranging from about 0° C. to 160° C., or to the boiling point of the solvent, may be used. Usually temperatures of from about 25° C. to about 120° C. are employed. Reaction times from about 2 hours up to 24 hours are usually adequate to complete the reaction.

The hydrolyzable silanes of the compositions described above possess unique properties that enable them to be formulated into the stable but reactive aqueous emulsions that impart water repellency and lubricity to surfaces to which they are applied without the use of organic solvents, which increase costs and may degrade the environment.

The silanes suitable for preparation of these aqueous emulsions must possess hydrolyzable groups that impart sufficient hydrophilicity to the silane to permit the initial emulsifiability in the aqueous medium, with or without the emulsifier. In the case of the preferred compositions described above, wherein R=$C_{18}$ alkyl and R'=methyl or ethyl, n must equal 2 or greater to produce aqueous emulsions with the proper emulsifier that exhibit long term stability. When n=0 or 1, a stable emulsion is not formed but rather an insoluble polymeric precipitate is produced by hydrolysis and condensation of the silane. For silanes with R=$C_8$ to $C_{18}$ hydrocarbon groups, stable emulsions may be prepared with n=2 or greater, however, for R=greater than $C_{18}$, n must be 3 or greater to achieve stable emulsions. Hydrolyzable groups other than those derived from polyether alcohols may be used to impart sufficient hydrophilicity to the silanes to permit stable aqueous emulsions to be formed. Hydrolyzable groups derived from polyalcohols may be used, however, they are generally more difficult or more costly to produce. The reaction of the polyalcohols with an alkyltrichlorosilane or alkyltrimethoxysilane to form the hydrolyzable silane structures frequently produces polymeric, crosslinked structures that possess significantly reduced water miscibility.

Emulsifiers usable to prepare the stable aqueous emulsions of the hydrolyzable silanes of this invention may be chosen from cationic, anionic, and non-ionic types. The preferred emulsifiers are those that have an HLB ("The HLB System" published by ICI America's Inc., Wilmington, Del.) value greater than 16, and preferably greater than 18. Emulsifiers with HLB values below 16 do not form stable aqueous emulsions with compositions of this invention. Mixtures of emulsifiers that each meet the above HLB requirements may be used, if they are compatible with one another. Suitable emulsifiers include, but are not limited to, $C_{8-18}$ alkyltrimethylammonium quaternary salts, alkali metal alkylbenzenesulfonates, linear alkyldiphenyletherdisulfonates, alpha-olefin sulfonates, alkyl and alkylether sulfates, $C_{12-18}$ alkyldimethylammonium salts, polyethoxylated $C_{12-18}$ alkylammonium salts and highly ethoxylated alkyl and arylalcohols. The type of emulsifier used may influence the magnitude of the desirable properties that are imparted to the substrates that are treated with the aqueous emulsions. Generally cationic emulsifiers that meet the above HLB requirements are preferred for preparing aqueous emulsions of the hydrolyzable silanes of this invention that will impart superior lubricity and scratch resistance properties to treated siliceous surfaces.

The aqueous emulsions of this invention are prepared by mixing the emulsifier with water and then slowly adding the silane, employing standard agitation techniques. After the materials are thoroughly blended, the emulsions must stand for a period of a few hours to several days, with or without further agitation, to permit the alkoxysilane to hydrolyze and the emulsion to achieve the stable equilibrium composition. The emulsions generally change from a clear colorless uniform mixture to a hazy or white milky emulsion during this standing period. The addition of an acid, such as a non-oxidizing organic acid like acetic acid, and/or the use of mild heating will accelerate the change to the stable equilibrium composition.

Analysis of the unique aqueous emulsions of this invention by nuclear magnetic resonance spectroscopy indicated that the alkoxysilanes have undergone hydrolysis to produce hydroxysilanes which are believed to possess the structure

$$R-Si(-OH)_3 \qquad (2)$$

and possibly low molecular weight oligomers thereof. However, unlike trihydroxysilanes in water mixtures without the proper emulsifier, these silanes do not undergo condensation to produce insoluble polymeric structures, but remain in a stabilized, emulsified state in the aqueous formulation. This hydrolysis in the aqueous emulsified state may require from a few minutes, for emulsions where the pH has been lowered to a value of 2 to 4 to hasten the reaction, to several days.

The stable aqueous emulsions may vary from a slightly hazy mixture to white milky formulations. Particle size measurements by light scattering techniques (Coulter N4MD instrument) have shown particle sizes of from less than 10 nm to about 300 nm. Most frequently the particle sizes range from less than 10 nm to about 100 nm, indicative of true microemulsions rather than emulsions.

The concentration of the emulsifier in the preferred emulsions is critical and varies with the particular emulsifiers and silanes. The optimum concentration for any given emulsifier/silane system is readily determined by routine procedures. In general, for the silanes of the present invention, the emulsifier may be present at concentrations of from 5 to 100, or more, weight percent based on the weight of the silane. The preferred concentrations of emulsifiers are in the range of about 10 to 50%. The concentration of the silane may be from 0.01 to 50% by weight, based on the total emulsion, preferably from 0.01 to 25 weight percent for practical reasons.

A uniform, hazy to milky appearance of an emulsion of this invention, with no separation of solids, is indicative of its stability. Poor stability is recognized by separation of the silane as a polymeric species due to condensation to form less soluble siloxane structures and/or gel formation. The preferred hydrocarbon silane emulsions of this invention containing an emulsifier are stable for over 6 months when stored at ambient temperatures. Many are stable at elevated temperatures of up to 60° C. and higher for over two months. Many emulsions, particularly when prepared at emulsifier levels of 30% or greater based on silane weight, are stable to alternate freezing and thawing conditions. Additionally, many of the emulsions are stable at pH levels as high as 11 or as low as 2, if the emulsifier is also unaffected by such conditions. The emulsions of this invention may also be diluted to 0.01% or lower without loss of stability.

The aqueous emulsified hydrocarbon silanes of this invention will interact with functional groups on the surface of substrates to produce a durable coating of the silane that imparts water repellency to those substrates. The hydrocarbon silane repellent treating compositions are most useful for imparting repellency and lubricity to substrates having siliceous, cellulosic or proteinaceous surfaces, and to polymer substrates having pendant active hydrogen groups, such as polyesters and polyamides. Typical of treatable substrates are wood, brick, concrete, masonry, stone, glass, ceramic tile, natural and synthetic fibers, fur, and leather.

In addition to this water repellency, hydrocarbon silane emulsions of this invention also impart enhanced lubricity to treated, smooth surfaces. The magnitude of this increased lubricity is generally proportional to the length of the hydrocarbon group, R. This enhanced lubricity of smooth surfaces that have been treated results in increased resistance of the surface towards scratching. This is a particularly important benefit for surfaces such as glass and ceramic tile.

The substrates are treated by coating the emulsions of this invention on the substrate surface and allowing the coated surface to dry. No special curing step is required to achieve the durable repellency and lubricity properties, however, heat may be applied to accelerate the drying process. The treated surface, after drying, may be washed with water to remove residual emulsifier and thereby increase the water repellency. The resultant product is a substrate having bonded thereto a surface layer of the hydrolyzed/condensed form of the compound of formula (1) and/or (2).

Various additives such as pigments and antioxidants may also be advantageously included in the emulsions of the present invention. It is also contemplated that mixtures of more than one silane compound may be used in the emulsions. In addition, it is also envisioned that the emulsions of this invention may be combined with other aqueous formulations to impart the unique properties of this invention to those formulations.

The following examples are presented to more fully demonstrate and further illustrate various individual aspects and features of the present invention. In doing so, the preferred hydrocarbon trialkoxysilanes are intentionally employed as being generally illustrative of the enhanced reactivity of the hydrolyzed emulsion compositions and generally illustrative of the resulting durable coatings of the process using these hydrocarbon silanes while being specifically illustrative of imparting useful and desirable repellency and or lubricity to substrate surfaces. As such, the examples are felt to be non-limiting and are meant to illustrate the invention, but are not meant to be unduly limiting in any way, particularly with respect to ultimate properties and utility of the coated surfaces.

EXAMPLE 1

Preparation of Octyltris(2-(2-methoxyethoxy)ethoxy)silane

To a dry flask fitted with an agitator, thermometer, additional funnel and reflux condenser was charged 222.8 g (0.90 mole) of octyltrichlorosilane and 225 g of heptane. The mixture was blanketed with nitrogen, heated to 80° C. and 333.7 g (2.78 mole) of 2-(2-methoxyethoxy)ethanol was added slowly over a 2 hour period. Hydrogen chloride was evolved from the mixture. After the addition was complete heating of the reaction was continued for 24 hours at 80° C. Then the solvent and all volatile components of the mixture were removed under vacuum, producing 451 g of the clear, colorless liquid product.

EXAMPLE 2

Preparation of Dodecyltris(2-(2-(2-methoxyethoxy)ethoxy)ethoxy)silane

The procedure of Example 1 was repeated with 151.8 g (0.50 mole) of dodecyltrichlorosilane and 200 g. of heptane. Under nitrogen 254.2 g (1.55 mole) of 2-(2-(2-methoxyethoxy)ethoxy)ethanol was added over 3 hours at 80° C. followed by heating of the reaction for an additional 48 hours. Vacuum stripping of all volatiles left 350 g of the clear, pale yellow liquid product.

EXAMPLE 3

Preparation of Octadecyltris(2-(2-(2-methoxyethoxy)ethoxy)ethoxy)silane

The procedure of Example 1 was repeated with 387.5 g (1.0 mole) of octadecyltrichlorosilane and 800 mL of heptane. Under nitrogen 508.4 g (3.10 mole) of 2-(2-(2-methoxyethoxy)ethoxy)ethanol was added at 80° C. over 4 hours. After heating the reaction for an additional 48 hours and removal of all volatile components under vacuum, 780 g of the pale yellow liquid product were obtained.

EXAMPLES 4–13

Aqueous Emulsions of Examples 1–3

The following aqueous emulsions of the silanes of Examples 1–3 were prepared by adding the silane slowly to a well agitated mixture of the emulsifier and acetic acid in water. The emulsions were agitated for 15 minutes after the addition of the silane, and the emulsions were allowed to stand for at least 72 hours to permit complete hydrolysis of the silane to occur and for the emulsion to achieve its equilibrium state. All emulsions were made at a concentration of 10 wt. % of the starting silane.

| Example | Silane | Emulsifier | Emulsifier Conc. (% of silane Wt.) | Acetic Acid* | pH |
|---|---|---|---|---|---|
| 4 | Ex. 1 | A | 40% | 10% | 2.6 |
| 5 | 1 | B | 30 | 5 | 3.5 |
| 6 | 1 | C | 40 | 10 | 3.5 |
| 7 | 1 | D | 40 | 15 | 3.5 |
| 8 | 2 | A | 40 | 5 | 2.6 |
| 9 | 2 | B | 30 | 5 | 3.5 |
| 0 | 2 | C | 40 | 10 | 3.5 |
| 11 | 2 | D | 40 | 15 | 3.0 |
| 12 | 3 | A | 40 | 10 | 2.4 |
| 13 | 3 | B | 30 | 5 | 3.5 |
| 14 | 3 | D | 40 | 15 | 3.5 |

*% based on weight of silane
Emulsifier
A = Hexadecyltrimethylammonium chloride
B = $C_{14-16}$ Alpha Olefin Sulfonate, sodium salt
C = Octadecylamine-60 E.O.
D = Octadecyldimethylammonium chloride

EXAMPLE 15

Lubricity of Treated Glass

The durable lubricity enhancing effects achieved by treating surfaces with compositions of this invention were demonstrated by measuring the static friction of glass slides that were treated with the aqueous emulsions of examples 4–14. For each of the emulsions of examples 4–14, 50×75 mm precleaned glass slides were treated by immersing them in the emulsion containing 0.1 wt. % of the silane. The slides were wiped dry with a lintless tissue and the static friction values measured. After the measurements were made, the slides were rinsed thoroughly with deionized water, dried and again the static friction values were determined.

The static friction values were determined by ASTM Method D 4518-91, Test Method A, using an inclined plane. Two treated glass slides were placed face to face on the level plane, a 500 g weight was placed on the slides to produce a force of 125 g per square inch of surface, and the inclination of the plane was increased at a rate of 14 degrees per minute. The static friction value was determined as the tangent of the angle at which the two slides just began to slide over each other. Triplicate values were determined for each of three pairs of slides for each treatment. The values shown in Table 1 show the excellent lubricating properties imparted by treatment with compositions of this invention. They also show a slight improvement in the lubricating values as the length of the R group of equation 1 is increased, and the influence that the emulsifier has on the lubricity properties achieved by the silane emulsions.

Each of the treated glass slides was then rated for its relative resistance to scratching by placing the slide on a weighing balance and using the corner edge of a new glass slide to scratch over the surface with a total force of 1000 g. The relative scratch resistance of the slides is also listed in Table I. A value of 1 indicates the most difficult to scratch. All treated slides were very difficult to scratch compared with untreated glass slides.

TABLE I

Static Friction and Scratch Resistance of Treated Glass

| Treatment | Static Friction Value | | Relative |
|---|---|---|---|
| Example | Unwashed | Water Washed | Scratch Resistance |
| 4 | 0.101 | 0.111 | 1 |
| 5 | 0.320 | 0.247 | 3 |
| 6 | 0.173 | 0.193 | 2 |
| 7 | 0.096 | 0.096 | 1 |
| 8 | 0.103 | 0.108 | 1 |
| 9 | 0.257 | 0.231 | 3 |
| 10 | 0.183 | 0.172 | 2 |
| 11 | 0.091 | 0.097 | 1 |
| 12 | 0.105 | 0.108 | 1 |
| 13 | 0.318 | 0.276 | 3 |
| 14 | 0.098 | 0.103 | 1 |
| Untreated | — | 0.348 | >>>3 |

EXAMPLE 16

Water Repellency

The water repellency properties that are imparted to surfaces treated with emulsions of Examples 5–14 were determined using 2"×2"×1.5" test pieces of concrete that were cut from standard 8"×16"×1.5" concrete patio blocks. The blocks were immersed for 10 minutes in the emulsions of Examples 5–14 which had been diluted to 2.5 wt. % of the starting silane. The excess emulsion was shaken from the concrete blocks and the blocks were allow to dry in ambient air for 24 hours. The blocks were then immersed in running water for 30 minutes to remove any residual emulsifier and allowed to dry for 72 hours. The water repellency of the treated blocks was then determined by placing a drop (approx. 3/16-inch, 5 mm diameter or 0.05 mL volume) of a test water solution on the blocks and observing the shape of the drop after 10 seconds. The test water solutions are a series of solutions numbered 1 through 8 containing isopropanol in water at concentrations of 2, 5, 10, 20, 30, 40, 50, and 60 volume percent isopropanol, respectively. The water repellency rating is the highest numbered test solution for which the drops remain spherical or hemispherical on the treated surface for at least ten seconds.

A second determination of water repellency of the same treated concrete blocks was made by placing a drop of deionized water on the block and estimating the contact angle of the drop. A contact angle of greater than 100 degrees was rated as Excellent, a contact angle of 80–100 degrees was rated as Good, an angle of 60–80 as Fair and an angle of less than 60 degrees as Poor.

TABLE II

Water Repellency Of Treated Concrete

| Treatment Example | Water Contact Angle | Water Repellency Rating |
|---|---|---|
| 5 | Excellent | 3 |
| 6 | Excellent | 3 |
| 7 | Excellent | 4 |
| 8 | Excellent | 3 |
| 9 | Excellent | 4 |
| 10 | Excellent | 4 |
| 11 | Excellent | 4 |
| 12 | Excellent | 3 |
| 13 | Good | 1 |
| Control | Poor | 0 |

EXAMPLE 17

Water Repellency of Treated Glass

To exemplify the water repellency that is imparted to glass by the emulsions of this invention, the water contact angles on treated glass slides were determined. Two 50×70mm precleaned glass slides were treated with the emulsion of Example 12 which had been diluted to 0.5 wt. % of the silane. The treatment involved dipping the glass slides into the emulsion, wiping them dry with a lintless tissue, then rinsing the slides with flowing deionized water and drying again. This treatment was repeated a second time on the two slides. One of the two treated slides was then washed with a standard laboratory glass cleaning detergent, rinsed with water and dried. The water contact angles were determined on both treated glass slides by the Sessile Drop method. The treated but unwashed slide had an advancing water contact angle of 102 degrees and a receding contact angle of 82 degrees. The slide which was treated and washed with the detergent had an advancing contact angle of 105 degrees and a receding contact angle of 82 degrees. These results illustrate the excellent water repellency of the glass surface that was achieved instantly by simple contact of the glass substrate with the emulsions of this invention, without additional curing of the treated substrate. This was due to the highly reactive nature of the emulsified silane composition. Additionally, the treatment was durable and could not be removed by washing with detergents, as one would expect for a silane composition that is chemically bonded to the substrate.

EXAMPLE 18

Durability of Surface Treatments

The durability of the treatments of glass surfaces with one of the emulsions of this invention was determined by measuring the change in the static friction value of a treated glass plate after it was boiled in water. Glass slides were treated by dipping in the emulsion of Example 12 which was diluted to 0.5%, and wiping until dry with a lintless tissue. The treated slides were then rinsed with deionized water for 15 seconds and then dried. The static friction was measured as in Example 15 above. Then the slides were boiled in deionized water for 30 minutes, dried, and the static friction values again determined. The slides were then boiled for an additional 90 minutes and the final static friction values determined. For comparison, the same sequence was carried out on untreated glass slides. The results shown in Table III illustrate that the benefits imparted by the emulsions of this invention are durable even under these extreme conditions.

TABLE III

| Minutes of Boiling Treatment | Static Friction Value | | |
|---|---|---|---|
| | 0 min. | 30 min. | 120 min. |
| None | 0.580 | 0.513 | 0.645 |
| Example 12 | 0.089 | 0.128 | 0.164 |

EXAMPLE 19

Stability of Emulsions

The emulsions of this invention are stable under ambient conditions for periods of at least 12 months. The stability under more extreme conditions is illustrated by this example. Four portions of the emulsion of Example 12 were prepared. The pH of two portions were adjusted from the original pH value of 2.5 to a value of 7.0 with acetic acid. One portion at pH 2.5 and one at pH 7.0 were stored in an oven at 80° C. for 6 days. No change in the appearance of the heated emulsions was observed during this period. After 6 days all four emulsions were diluted to 0.1% and glass plates were dipped into the emulsions and wiped dry with lintless tissues. The treated plates were rinsed with water, dried, and the static friction values determined as in Example 15. The values for the static friction shown in Table IV illustrate the excellent stability of the emulsions of this invention.

TABLE IV

Emulsion Stability

| Emulsion pH | Storage Conditions | Static Friction Value of Treated Glass Slides |
|---|---|---|
| 2.5 | Room temperature | 0.096 |
| 2.5 | 80° C./6 days | 0.106 |
| 7.0 | Room temperature | 0.094 |
| 7.0 | 80° C./6 days | 0.107 |

Having thus described and exemplified the invention with a certain degree of particularity, it should be appreciated that the following claims are not to be so limited but are to be afforded a scope commensurate with the wording of each element of the claim and equivalents thereof.

I claim:

1. A reactive aqueous emulsion comprising: (a) an alkoxysilane compound emulsified in water, wherein said alkoxysilane compound is represented by the formula:

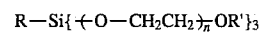

R—Si{(—O—CH$_2$CH$_2$)$_n$OR'}$_3$ where: R is a hydrocarbon radical of 8 to 24 carbons; R' are the same or different alkyl radicals of 1 to 3 carbon atoms; and n=2 to 10 and (b) an effective amount of an emulsifier of sufficiently high HLB value to simultaneously retain said alkoxysilane compound in a hydrolyzed state and inhibit the resulting hydrolyzed alkoxysilane compound from self-condensation.

2. A reactive aqueous emulsion of claim 1 wherein R is a hydrocarbon radical with 16 or greater carbons.

3. A reactive aqueous emulsion of claim 1 wherein said hydrolyzed alkoxysilane compound is octyltris(2-(2-methoxyethoxy)ethoxy)silane.

4. A reactive aqueous emulsion of claim 1 wherein said hydrolyzed alkoxysilane compound is dodecyltris(2-(2-(2-methoxyethoxy)ethoxy)ethoxy)silane.

5. A reactive aqueous emulsion of claim 1 wherein said hydrolyzed alkoxysilane compound is octadecyltris(2-(2-(2-methoxyethoxy)ethoxy)ethoxy)silane.

6. A process for coating a substrate comprising the steps of:

(a) emulsifying in water (i) an alkoxysilane compound represented by the formula:

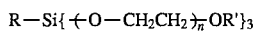

where: R is a hydrocarbon radical of 8 to 24 carbons; R' are the same or different alkyl radicals of 1 to 3 carbon atoms; and n=2 to 10 and (ii) an effective mount of an emulsifier of sufficiently high HLB value to simultaneously retain said alkoxysilane compound in a hydrolyzed state and inhibit the resulting hydrolyzed alkoxysilane compound from self-condensation thus forming a reactive aqueous emulsion; and (b) contacting a substrate with said reactive aqueous emulsion of step (a).

7. A process for coating a substrate according to claim 6 wherein R is a hydrocarbon radical with 16 or greater carbons.

8. A process for coating a substrate according to claim 6 wherein said hydrolyzed alkoxysilane compound is octyltris(2-(2-methoxyethoxy)ethoxy)silane.

9. A process for coating a substrate according to claim 6 wherein said hydrolyzed alkoxysilane compound is dodecyltris(2-(2-(2-methoxyethoxy)ethoxy)ethoxy)silane.

10. A process for coating a substrate according to claim 6 wherein said hydrolyzable alkoxysilane compound is octadecyltris(2-(2-(2-methoxyethoxy)ethoxy)ethoxy)silane.

* * * * *